Figure 1:
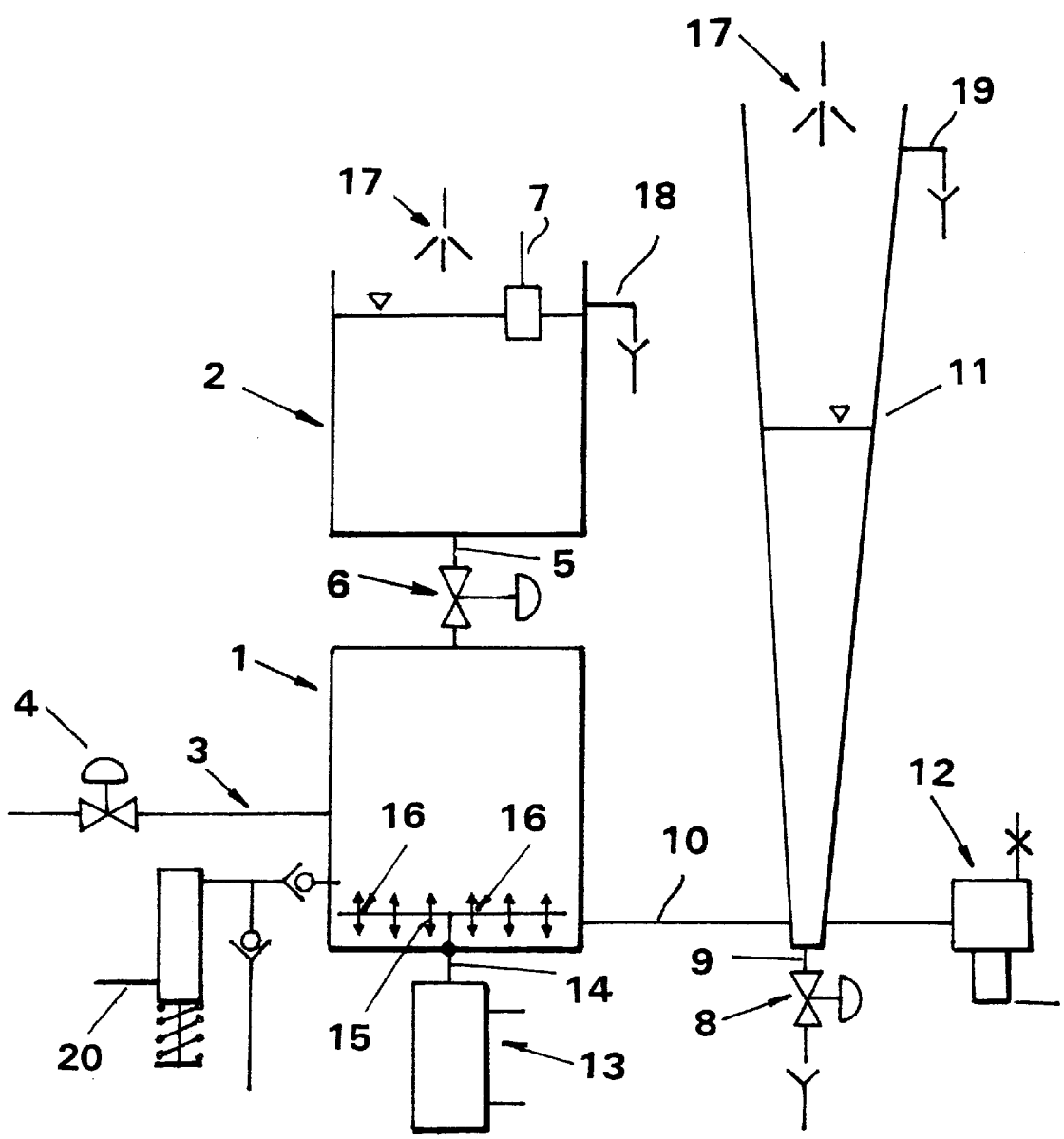

United States Patent
Fladda et al.

[11] Patent Number: 6,124,111
[45] Date of Patent: Sep. 26, 2000

[54] METHOD AND AN ARRANGEMENT FOR MEASURING THE AMOUNT/ACTIVITY OF CATALASE BEFORE OR IN CONNECTION WITH BLEACHING OF PREFERABLY CELLULOSE FIBRES INCLUDED IN A PULP SUSPENSION

[75] Inventors: Gerdt Fladda, Taby; Stig Norder, Saffle; Bertil Olsson, Nol, all of Sweden

[73] Assignee: BTG Kalle Inventing AB, A Corp., Sweden

[21] Appl. No.: 09/367,653

[22] PCT Filed: Dec. 22, 1998

[86] PCT No.: PCT/SE98/02434

§ 371 Date: Aug. 19, 1999

§ 102(e) Date: Aug. 19, 1999

[87] PCT Pub. No.: WO99/35482

PCT Pub. Date: Jul. 15, 1999

[30] Foreign Application Priority Data

Dec. 23, 1997 [SE] Sweden .................................. 9704872

[51] Int. Cl.⁷ .............................. C12Q 1/30; C12Q 1/00; C12Q 1/28
[52] U.S. Cl. ............................ 435/27; 435/4; 435/283.1; 435/28; 536/56; 422/50; 422/68.1
[58] Field of Search ............................... 435/27, 4, 283.1, 435/28; 536/56; 422/50, 68.1

[56] References Cited

FOREIGN PATENT DOCUMENTS

| 0661403 | 7/1995 | European Pat. Off. ........ D12C 9/153 |
|---|---|---|
| 2269191 | 2/1994 | United Kingdom ............. D12C 9/10 |
| 9830884 | 7/1998 | WIPO .............................. G01N 7/18 |
| 99/35482 | 7/1999 | WIPO . |

Primary Examiner—Louise N. Leary
Attorney, Agent, or Firm—Ostrolenk, Faber, Gerb & Soffen, LLP

[57] ABSTRACT

The invention relates to a method and a device for measuring the amount/activity of the enzyme catalase before or in connection with bleaching of cellulose fibers preferably in a pulp suspension for the purpose of providing a better and more uniform product quality and a correct dosing of the actual bleaching substance during the bleaching. According to the invention a measurement sample is derived from a predetermined volume of the pulp suspension after or during the bleaching. Further, a determined amount of bleaching substance is added to the sample, which is agitated so that the bleaching substance is decomposed and oxygen gas is generated, which oxygen gas pushes out a certain sample volume from the measurement sample, which sample volume is measured after a determined time and is directly or indirectly converted, e.g. via a simple algorithm, to a value representing the actual amount of catalase.

7 Claims, 1 Drawing Sheet

METHOD AND AN ARRANGEMENT FOR MEASURING THE AMOUNT/ACTIVITY OF CATALASE BEFORE OR IN CONNECTION WITH BLEACHING OF PREFERABLY CELLULOSE FIBRES INCLUDED IN A PULP SUSPENSION

The present invention relates to a method and a device for measuring the quantity/activity of the enzyme catalase before or during bleaching preferably of cellulose fibres in a pulp suspension in providing a better and more uniform product quality and a correct dosing of the bleaching chemical used.

In the pulp and paper industry the bleaching of cellulose fibres is essential to the final product quality. Principally, the bleaching has two aims, namely first to create a continuation of the lignin-separating process, which consists of cooking in the manufacture of chemical pulps, and second to remove the dark colour given to the pulp by certain organic substances so that a certain brightness is created. Previously a method is known for measuring of the content of chemicals during bleaching of cellulose fibres in forest industry processes. Said method is based on that the enzyme catalase is added to the measurement sample, whereby said bleaching chemical is decompositioned and a gas is formed. The quantity of gas is then a measure on how much of said bleaching chemical existing in the sample. The gas quantity is measured by a special device based on a manometric method. The method has shown to function excellent for e.g. peroxide, which today is a very common bleaching chemical in connection with the forest industry. Here, it is important to measure the content of peroxide which remains after the bleaching process, i.e. the content of residual peroxide. This has a great importance for the fibre quality achieved.

In the pulp processes where microbiological activity exists principally during the production of recycle fibres, the enzyme catalase is produced from certain microorganisms.

Exactly as in the method described above then the peroxide is decomposed into water and oxygen gas, the amount of peroxide in the fibre suspension being decreased. This is a process technical worry. An indication of the content/activity of catalase shoud open possibilities to act.

The object of the present invention is to provide method and a device of the type mentioned above, by means of which method and device the disadvantages above referred to are eliminated. The features characterizing the invention appear from the subsequent patent claims.

Thanks to the invention there do now exist a method and a device yielding a quick result, whereby an indication is obtained about how large content/activity of catalase a fibre suspension contains before or in connection with the bleaching, so that a compensation can be made for that during the calculation or measuring of the content of chemicals-residual peroxide during the bleaching in achieving of a final result as correct as possible.

An embodiment exemplifying the intention of the invention will now be described in greater detail, reference being made to the accompanying drawing, which is a diagrammatic view of a measurement device according to the present invention.

The method according to the invention is based on the fact that the instability of the bleaching chemical to easily decompose is taken care of, whereby oxygen gas is formed if the enzyme catalase exists. By adding a certain amount of bleaching substance, preferably peroxide, to a sample having a predetermined volume taken from the pulp suspension, before or during the bleaching of cellulose fibres in a pulp suspension, now a measure/activity of catalase exsisting in the suspension instead of residual peroxide can be achieved.

The filtrate from the fibre suspension, which can contain catalase, is added to the measurement container of the measuring device. In stead of dosing of catalase into the sample, as during determining of peroxide, now a predetermined amount of peroxide is dosed. Hereafter principally the normal measurement sequence follows with stirring and measuring. Presence of catalase in the measurement sample gives a decomposition of the peroxide dosed and the gas amount formed hereby is a measure on the content/activity of catalase. A certain fault-measuring could happen if the sample is not only containing catalase but also a certain amount of residual peroxide. This can be corrected e.g. by alternately measuring of catalase (=dosing of peroxide) and amount of residual peroxide (=dosing of catalase).

The new measurement method is thus based on the well-known instability of the bleaching chemical meaning that it together with the enzyme catalase easily decompose, oxygen being generated in the process. Measurement of the oxygen gas content then represents a measure of the quantity/activity of catalase in the sample. The oxygen gas content can suitably be determined according to a manometric method, eg. by registration of the pressure build-up, inside a closed measurement container.

When the oxygen gas content is to be measured the sample is normally enclosed in a measurement container, a determined quantity of bleaching substance, e.g. peroxide, is dosed and the overpressure caused by the oxygen gas generation is measured. Alternatively, the oxygen gas generated is caused to push a corresponding amount of the liquid (sample) into an open vessel, communicating with the measurement vessel. The liquid level in the communicating vessel will then be the measure of the quantity/activity of the enzyme catalase. The liquid level is measured by means of a pressure sensor installed at the bottom of the level vessel. In addition thereto the vessel can be given such a shape that the level is e.g. a logarithmic signal representing the quantity/activity of catalase. This means that the instrument can operate within a wide measurement range maintaining, as a matter of principle, the same accuracy without the need of any changes in the instrument.

Another advantage of using a communicating measurement vessel is that it will become simpler automatically to diagnose a defect in the measurement signal and to carry out an automatic calibration of the pressure sensor and hence of the amount/activity of catalase.

FIG. 1 does diagrammatically show the structure of the measurement system according to a preferred embodiment of the invention. It does diagrammatically explain the mode of operation of an instrument which can be used, based on the method according to the invention, for measurement of the amount/activity of catalase. The device for carrying out a measurement according to the invention comprises a measurement container 1 and a container 2, the container 1 serving as a reaction chamber and the container 2 as an overflow vessel. The sample on which the measurement is to be made enters the container 1 through a pipe 3 via a valve 4. The containers 1 and 2 are interconnected by a pipe 5, which likewise is provided with a valve 6 for cutting off the connection between the containers 1 and 2. When a measurement is to be made the valves 4 and 6 are opened, whereupon the sample in question flows into the containers 1 and 2 up to the activation level for a switch 7 in the container 2 so that the valves 4 and 6 are again closed. During the filling period a valve 8 is closed, which is connected in an outlet pipe 9 below a level vessel 11, 10 which via a pipe 10 communicates with the container 1. This means that also the communicating level vessel 11 will be filled with sample liquid. When the valve 8 is opened the vessel 11 is emptied, whereupon the valve 8 is closed. The emptying of the level vessel 11 does not affect the contents of the container 1. This is due to the relatively small, about 6 mm, cross-section of the pipe 10 between the container 1 and the vessel 11. Thanks to the surface tension of the sample liquid there cannot in the pipe 10 or in its opening be formed an air bubble that could rise towards the upper portion of the container 1 and push out the sample from the container. Further, the negative pressure in the container 1 prevents out-through of the sample therein. Next, there is added a certain amount of a bleaching substance i.e. peroxide, with the aid of a dosage device 20 connected to the container 1, which causes a corresponding sample volume to be pressed out from the container 1 into the connection pipe between the container 1 and the level vessel 11, which is filled up to a minimum level. This means that a pressure sensor 12 connected to the level vessel will always indicate a certain pressure before the measurement clearly representing the zero point for the measurement and at the same time providing a possibility for a certain function checking (self-diagnostics).

After the dosage the bleaching substance is mixed with the sample by means of a special agitator 13 located below the container 1 and comprising a rod supporting a disc 15, the diameter of which is slightly less than the inner diameter of the container 1. The disc 15 has a number of through holes 16 and can reciprocate up and down, inside the container 1 thus initiating decomposition of the peroxide into water and oxygen gas. The oxygen gas thus formed pushes a corresponding sample volume out from the container 1 and into the level vessel 11 and the changed liquid column level is indicated via the pressure sensor 12. Normally, the reaction is rather rapid initially when most of the peroxide is deposed. After some time the reaction is substantially finished, the liquid level in the vessel 11 has a constant position and the pressure signal is in a simple algorithm converted to a value for the amount/activity of catalase expressed in ppm or mg/l. The measurement system is then emptied in the way that the valves 6 and 8 are opened after which the system is cleaned by means of special spray nozzles 17 for clean water, whereupon the next measurement can be started. All of the measuring sequence is controlled by a micro processor system (not shown in the drawing) also handling data collection, result calculation, result presentation and self-diagnostics with an alarm function.

The following comments also relate to how to carry out the method with the aid of the device according to the present invention. The reaction velocity is strongly dependent on the stirring of the sample when peroxide is decomposed by presence of catalase or rather by the amount of mechanical energy transferred to the sample. The reason for this is that due to charging phenomena the catalase will rather quickly be surrounded by water molecules preventing the catalase from being an active catalyst in the decomposition of the added peroxide into water and oxygen gas. These catalase-water bindings are strong and can be broken only via a powerful mechanical influence. According to the invention this is achieved by means of the special agitator 13. Its disc 15 reciprocates rapidly up and down inside the reaction chamber or the first measurement container 1, usually at a frequency of a few dozen movements per minute. The disc 15 is driven by a pneumatic, linear cylinder and its diameter is only a few millimeters less than the inner diameter of the container 1. Accordingly, the stirring action is essential to reach a good measurement result.

The reaction chamber, or the measurement container 1, preferably has a volume of about 400 ml. The height of the container 1 roughly equals its diameter. This has a certain significance as far as the agitation is concerned. The container volume can naturally be varied but it should be borne in mind that the volume should not be that small that the accuracy and the resolution of the measuring method are lost due to the small amounts of oxygen gas generated when the peroxide is decomposed. A greater volume gives a more robust structure, which furthermore is less sensitive to contamination etc.

The second measurement container 2 and the level vessel 11 are each provided with an overflow outlet 18, 19, respectively, so that the sample liquid can be diverted to sewer in case of system failure.

When greater temperature variations in the reaction chamber or in the container 1 are expected the equipment should include a temperature sensor correcting gas volume changes. The pressure sensor 12 at the level vessel 11 could be a standard sensor having a good temperature compensation.

What is claimed is:

1. A method for measuring the amount/activity of the enzyme catalase before or during bleaching of cellulose fibres, in a pulp suspension, for the purpose of providing an improved and more uniform product quality and a correct dosing of actual bleaching substance during the bleaching, characterized in that a sample having a predetermined volume is taken from the pulp suspension after or during the bleaching, that a determined amount of bleaching substance is added to the sample, that the sample is stirred to cause a decomposition of the bleaching substance and formation of oxygen gas, whereby the oxygen gas thus formed will form the sample push out a certain sample volume, said pushed out sample volume being measured after a predetermined time and being directly or indirectly, e.g. via a simple algorithm, converted to a value representing the content of the bleaching substance used and measurement of the amount/activity of the catalase enzyme.

2. The method as claimed in claim 1, characterized in that to the sample there is dosed a peroxide bleaching chemical.

3. The method as claimed in claim 1, characterized in that the sample volume pushed out from the sample is collected in a level vessel communicating with a measurement container containing the sample.

4. A device for measuring the content of chemical substances or the amount/activity of the enzyme catalase before or in connection with bleaching of cellulose fibres, in a pulp suspension, for the purpose of providing an improved and more uniform product quality and a correct dosing of actual bleaching substance during the bleaching, characterized in a reaction chamber or measurement container (1), having a dosage device (20) for the addition of a determined amount of a bleaching substance and said container (1) is connected to a vessel (11) communicating with it and adapted to receive the amount of sample liquid corresponding to the gas volume, which is generated at the decomposition of the bleaching substance and which pushes out the sample liquid from the container (1), which exhibits agitation means (13) for effecting a mixing of the sample and a decomposition of the bleaching substance dosed into the same.

5. The device as claimed in claim 4, characterized in that the agitation means (13) is constituted by a disc (15), the diameter of which is slightly less than the inner diameter of the measurement container (1), said disc (15) having a number of through holes (16) and being movable inside the container (1) in an upward and downward direction.

6. The device as claimed in claim 4, characterized in that a pressure measuring sensor (12) is connected to the level vessel (11) for the purpose of indicating changes of the level of the liquid column in the level vessel (11), which appear during the measurement.

7. The device as claimed in claim 4, characterized in that the communicating level vessel (11) communicates with the measurement container via a connection pipe (10) having a relatively small opening, which due to the surface tension in the actual sample liquid and to negative pressure in the measurement container (1), respectively, does not affect the contents of the container (1) upon emptying of the level vessel (11).

* * * * *